United States Patent [19]
Paradis

[11] Patent Number: 5,289,849
[45] Date of Patent: Mar. 1, 1994

[54] CONTROL OF FLUID FLOW

[76] Inventor: Joseph R. Paradis, 17 Hickory Forest Dr., Hilton Head Island, S.C. 29926

[21] Appl. No.: 871,190

[22] Filed: Apr. 20, 1992

Related U.S. Application Data

[63] Continuation-in-part of Ser. No. 530,097, May 29, 1990, Pat. No. 5,070,905, and a continuation-in-part of Ser. No. 804,811, Dec. 9, 1991, Pat. No. 5,190,067.

[51] Int. Cl.$^5$ .................. A61M 5/14; F16K 15/14
[52] U.S. Cl. .................. 137/606; 251/149.1; 604/83
[58] Field of Search ............ 251/149.1; 137/606; 604/83, 86, 167

[56] References Cited

U.S. PATENT DOCUMENTS

| | | | |
|---|---|---|---|
| 4,000,740 | 1/1977 | Mittleman | 604/86 |
| 4,405,316 | 9/1983 | Mittleman | 604/86 |
| 4,429,856 | 2/1984 | Jackson | 251/149.1 |
| 4,915,687 | 4/1990 | Sivert | 251/149.1 X |
| 5,064,416 | 11/1991 | Newgard | 251/149.1 X |
| 5,070,905 | 12/1991 | Paradis | 137/606 |
| 5,116,021 | 5/1992 | Faust | 251/149.1 |

Primary Examiner—Robert G. Nilson
Attorney, Agent, or Firm—George E. Kersey

[57] ABSTRACT

A flow control device with at least one flow channel in a housing that can contain an injection site and/or a pre-biased flow control diaphragm that is stabilized by a flexible contact member. Any flow channel, including that with an injection site, may include a plug acted upon by an external actuator, which can be self-sealing. The injection site with a flexible plug can be used for needleless infusion of fluids, or the flexible plug may be used with a needle for the conventional injection of fluid.

18 Claims, 16 Drawing Sheets

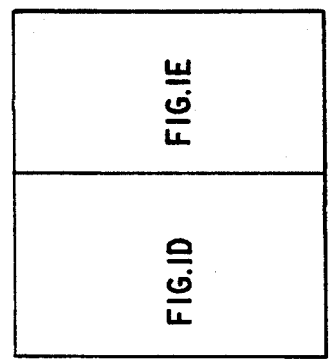
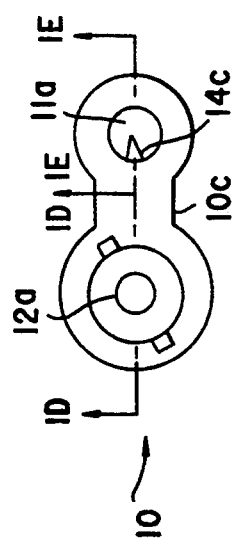
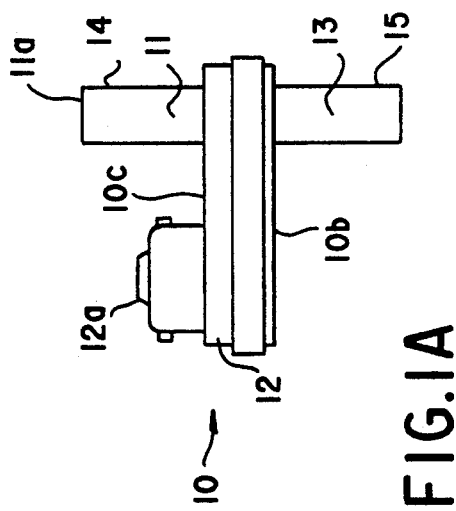

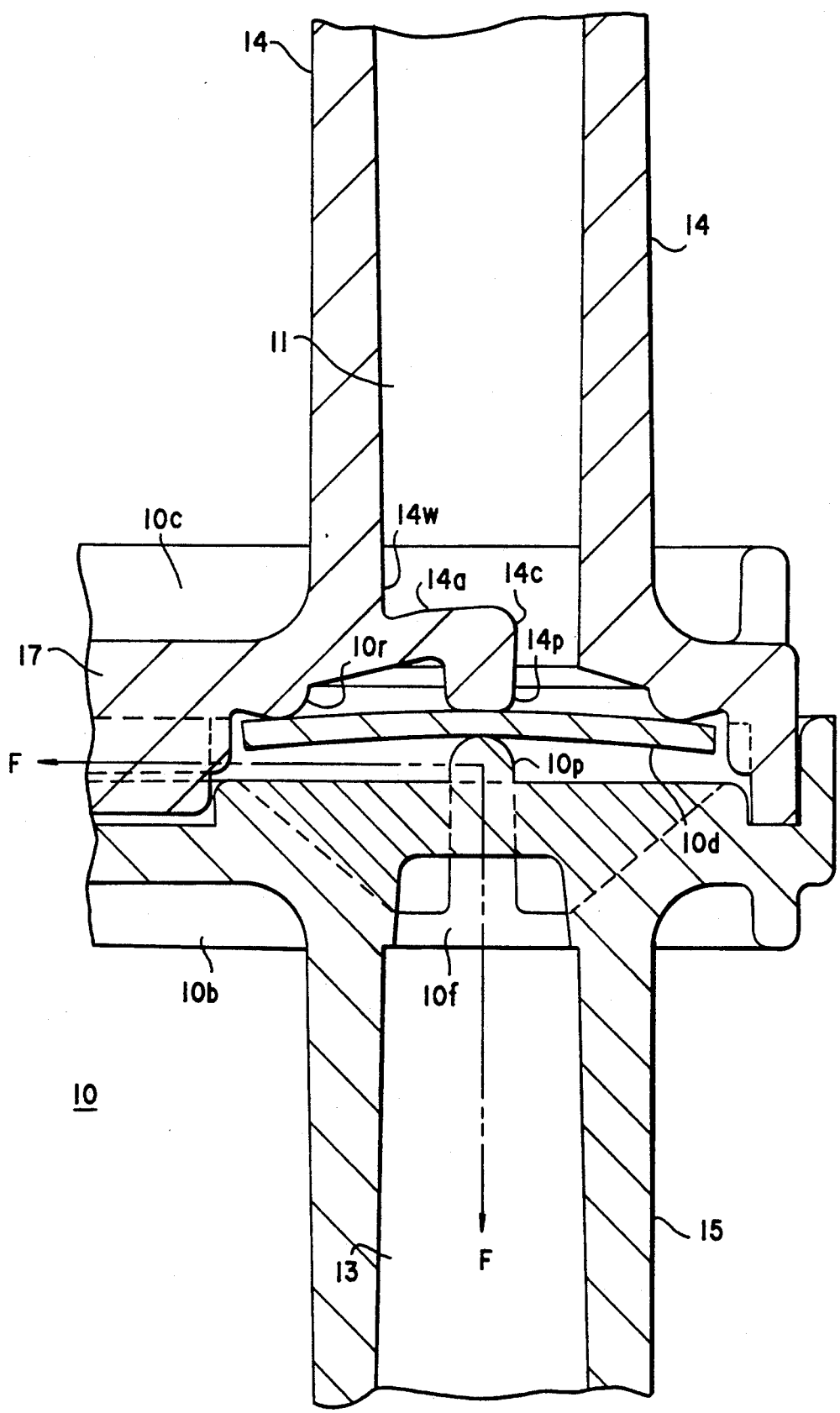
FIG.IE

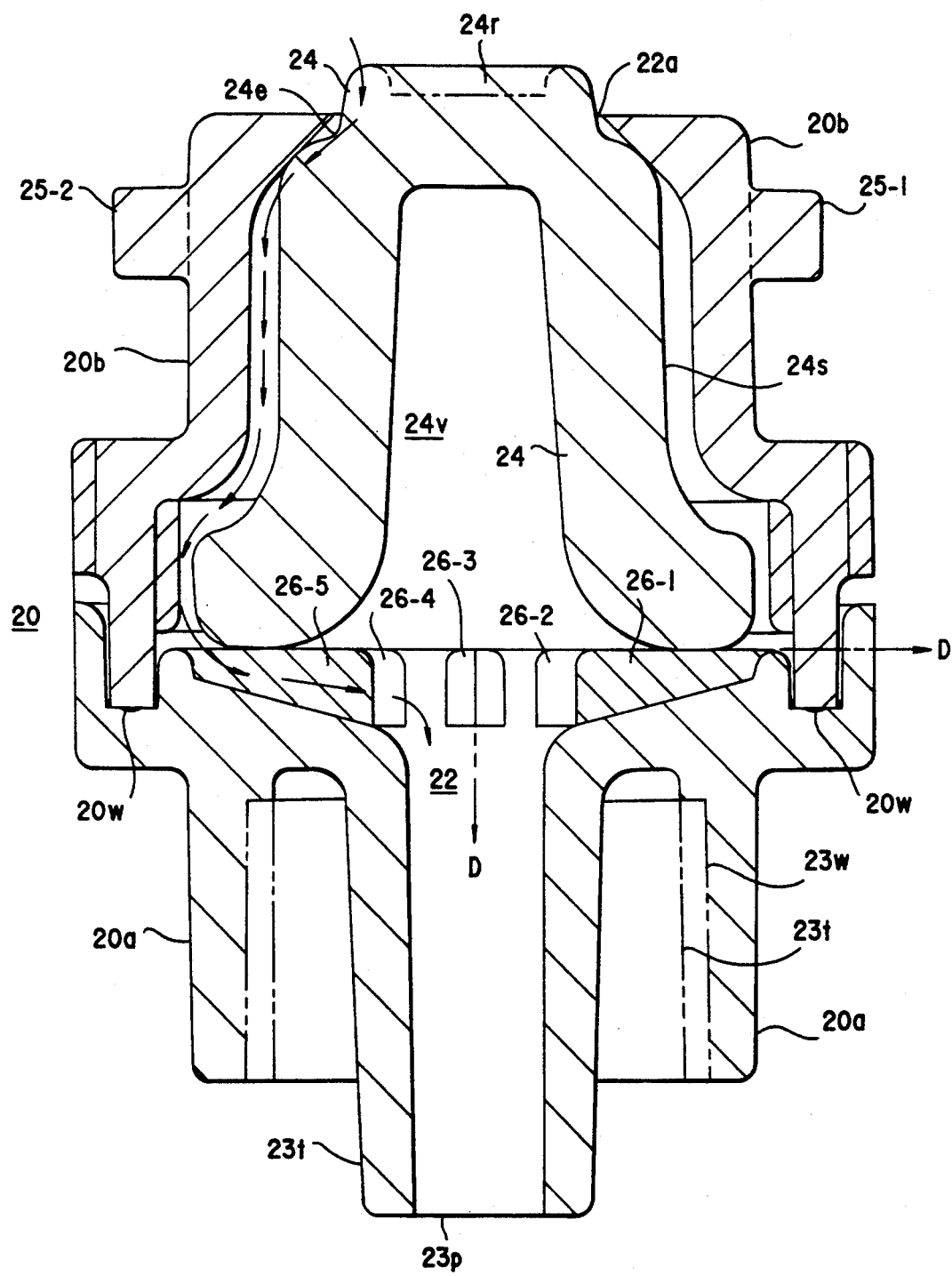

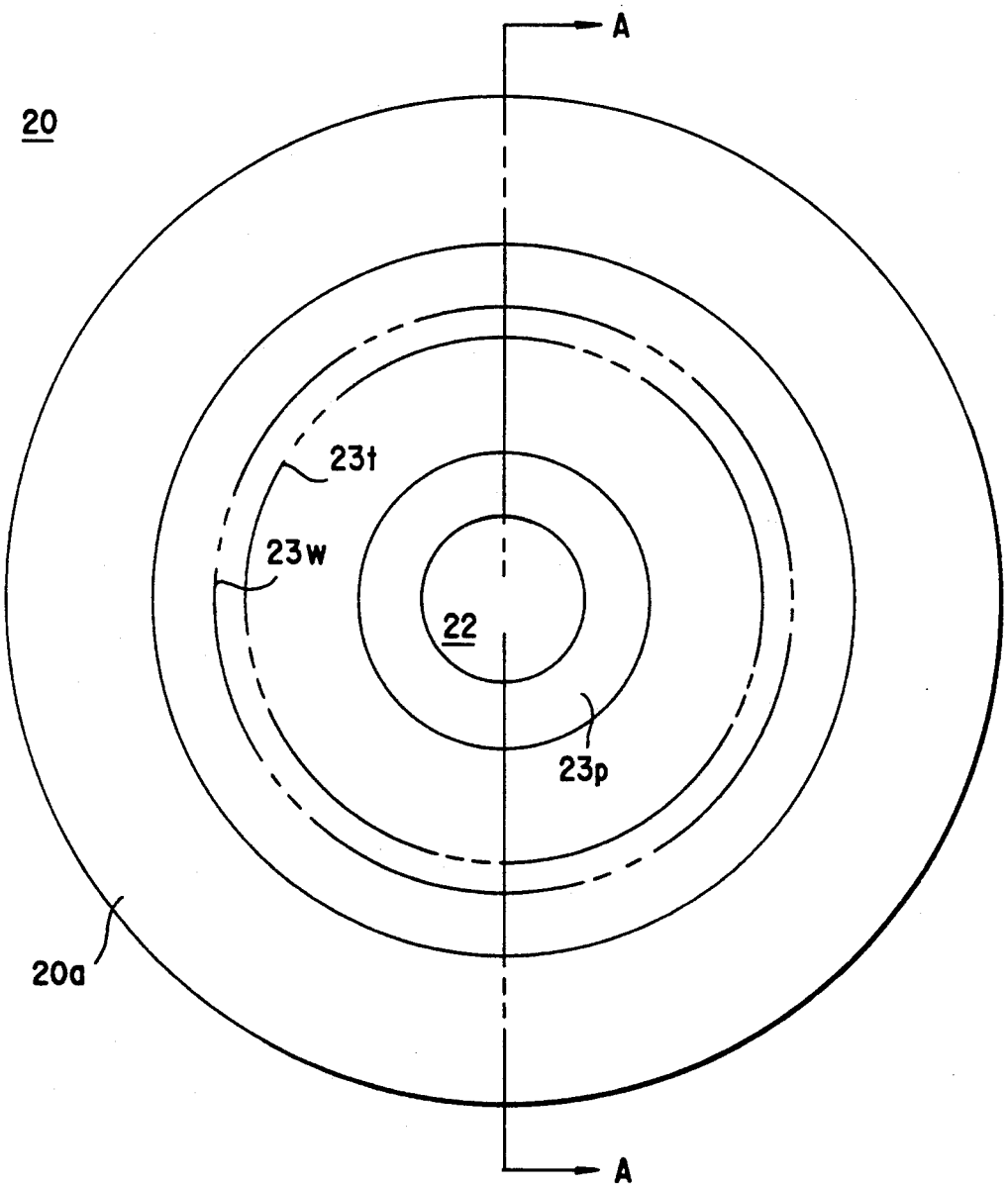

FIG.3D
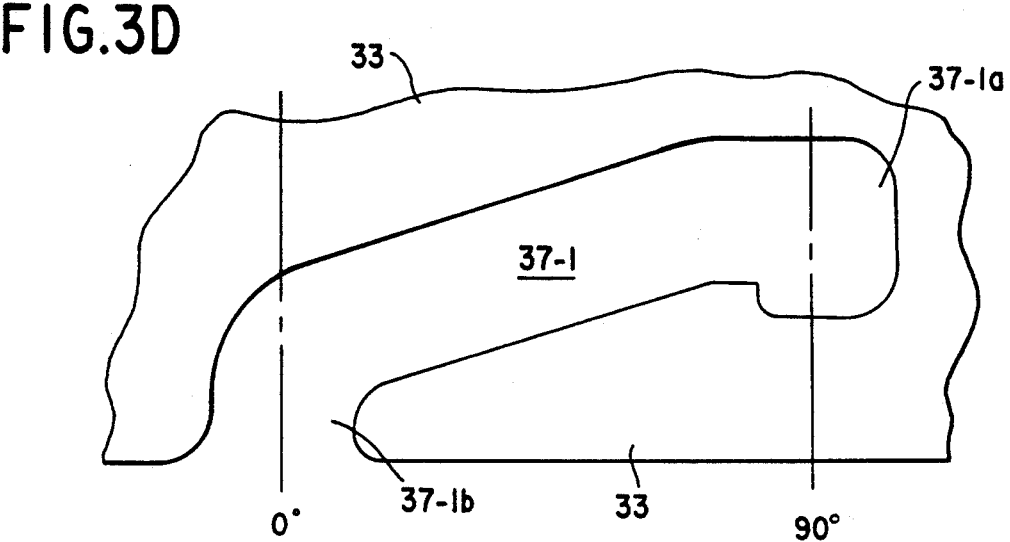
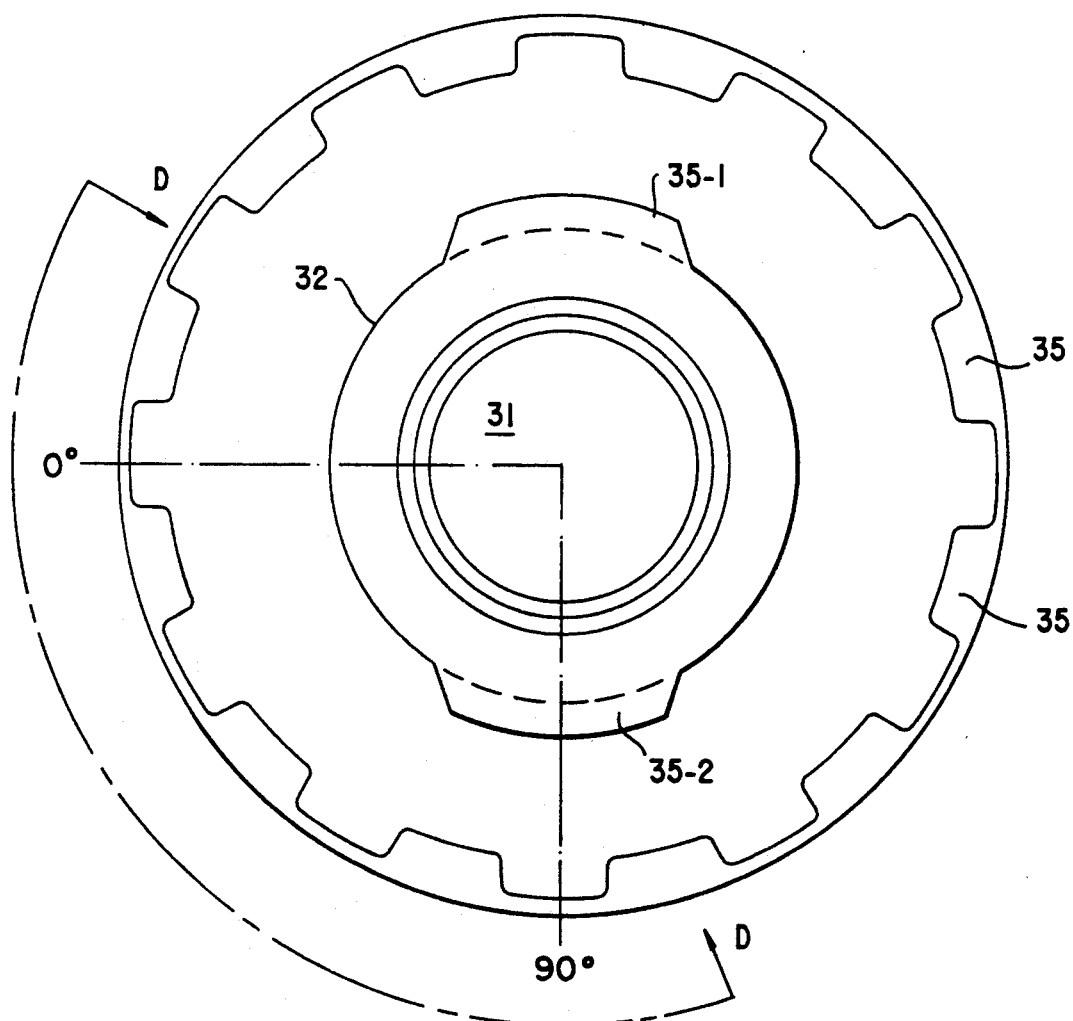
FIG.3E

CONTROL OF FLUID FLOW

BACKGROUND OF THE INVENTION

This is a continuation-in-part of Ser. No. 07/530,097 filed May 29, 1990, now U.S. Pat. No. 5,070,905, issued Dec. 10, 1991 and Ser. No. 07/804,811 filed Dec. 9, 1991, now U.S. Pat. No. 5,190,067. This invention relates to flow control and more particularly, to the needleless infusion and combining of fluids.

It often is desirable to control the flow of fluid such as liquids and gases. A common device for that purpose is known as a "check" valve. The check valve functions by the deflection of an elastomeric element towards and away from a valve seat. The deflection is towards the valve seat in order to prevent flow, and away from the seat to permit flow.

Another common device is a "Y" fitting which can include a check valve in one branch of the "Y" and an injection site in another branch.

In some cases the control of fluid flow is with respect to a multiplicity of channels that have varying degrees of convergence with one another. A typical multichannel arrangement makes use of connectors which permit the intercoupling of flow channels as desired. For example, when two channels are to be joined selectively to permit a common output from a single channel, the connector can take the form of a fitting that resembles a "Y".

The inclusion of control valves in the various lines leading to a coupler can pose a number of complications. The inclusion of separate control elements can cause difficulties in assuring proper sealing. A common point of leakage in a line often occurs where the line has been severed in order to receive a control element. In addition, the inclusion of separate control elements in various lines leading to a coupler does not always provide the most efficient control over fluid flow.

One solution for overcoming difficulties associated with prior art valves that control flow on multiple channels is set forth in U.S. Pat. No. 4,610,276 ("'276") which issued Sep. 9, 1986. This patent discloses a directional flow control valve with a main channel for the through-flow of fluid, and a branch channel connected to the main channel at an intermediate position. This permits the convergence of flow through the main channel with flow through the branch channel. At the convergence of the two channels, there is a diaphragm for controlling the flow between the two channels. The diaphragm is clamped and bowed under pressure into the inlet of the branch channel. The application of pressure to the diaphragm assures the sealing of the branch channel against flow diverted from the main channel.

There also is a common housing in the '276 patent for the main flow channel and the branch flow channel. The diaphragm is bowed into the branch channel by a set of prongs with tips that extend as projections from a shelf that is common to the branch and main channels. The bowing of the diaphragm is asymmetric, and greater pressure is applied away from the region of outflow from the branch channel.

While the diaphragm of the '276 patent operates properly in most cases, there is the possibility that the diaphragm will fail to seat properly.

Another valve arrangement for dealing with main and branch channels is disclosed in U.S. Pat. No. 4,874,369 which issued Oct. 17, 1989. This arrangement employs an injection site in conjunction with a valve, illustratively of the duck-bill type, in a configuration that is complex, costly and difficult to manufacture. In addition, duck-bill valves of the type contemplated by the '369 patent have proved to be unreliable in practice, with such difficulties as failure to seal properly.

Other arrangements which relate to the control of fluid flow are disclosed in Osborne U.S. Pat. No. 2,270,468; Goott et al U.S. Pat. No. 3,370,305; Craft U.S. Pat. No. 3,457,933; Rosenberg U.S. Pat. Nos. 3,572,375, 3,650,093 and 3,710,942; Bobo U.S. Pat. No. 3,886,937; Melnick U.S. Pat. No. 3,891,000; Mittleman U.S. Pat. Nos. 4,000,740 and 4,405,316; Stevens U.S. Pat. No. 4,000,739; Zedes et al U.S. Pat. No. 4,005,710; Mittleman et al U.S. Pat. Nos. 4,048,996 and 4,133,441; Rushkie et al U.S. Pat. No. 4,222,407; Sheehan et al U.S. Pat. No. 4,294,249; Spademan U.S. Pat. No. 4,338,934; Paradis U.S. Pat. No. 4,415,003; Spector et al U.S. Pat. No. 4,424,833; Edwards et al U.S. Pat. No. 4,566,493; Goodell U.S. Pat. No. 4,596,265; Suzuki et al U.S. Pat. No. 4,610,674 and Holtermann et al U.S. Pat. No. 4,958,661; EPO 0109903; France 2004771 and UK 2033230. None of these arrangements provide enhanced flow control where there is diversion of fluid flow from one direction to another.

In addition, all of the foregoing valves require the presence of fluid pressure in order to operate a flow control member, such as a diaphragm, either by exerting pressure to open the control member, or by using reverse pressure to close the control member. In some cases it is desirable to be able to act upon the control member by using other than fluid pressure. Thus, a user may want to actuate the control member independently of the presence of fluid pressure, in preparation for anticipated fluid flow. In other cases, it is desirable to maintain a control member in its open position for a prescribed interval of time independently of whether fluid flow is present.

Another consideration that applies in the use of flow control devices is that the fittings used with the devices vary in tolerances. As a result, flow control valves are employed with a variety of fittings. A flow control valve that is suitable for a particular fitting may not function in the same way with a different fitting, even if the fitting is of the same general type, because of tolerance variations.

Still another consideration applies to flow control devices that are intended to operate with low "cracking" pressures, i.e. the pressure at which a control diaphragm moves away from its seat. For such devices, it is desirable to use relatively thin diaphragms. Unfortunatley, thin diaphragms pose problems of stability. The diaphragm may move slightly away from its central position against a side wall, and because of the thinness of the diaphragm, may tend to stick, causing a problem of leakage.

One attempt to stabilize diaphragms is disclosed in Raines U.S. Pat. No. 4,535,820 which issued Aug. 20, 1985. In Raines, the diaphragm is held in place by a transverse bar that extends completely across the valve body and opposite a triangular support. The latter partially deforms the center of the diaphragm in an attempt to restrain the diaphragm against inadvertent sideways movement.

The deformation of the diaphragm is undesirable as it introduces other problems, such as interference with proper sealing and subsequent operation.

Another objection to existing arrangements is that their activators are not interchangeable. Thus injection sites that require needle injection cannot be used without needles; conversely injection sites that are externally actuated by inserting a member that opens a diaphragm cannot be used with needles. In addition, non-needle injection sites present problems of sterility. In order to have external access to the control diaphragm, it is necesary to have an open channel that can become contaminated. Even when a temporary seal is provided for the open channel, removal of the seal prior to injection allows inadvertent contamination. This is by contrast with an injection site having a needle-puncturable surface. The latter can be wiped clean with a sterilizing agent before injection is to take place.

Accordingly, it is an object of the invention to enhance the control that can be achieved over fluid flow. A related object is to enhance flow control where fluid infusion or combination is to take place. Another related object is to enhance flow control where fluid flow is diverted in direction.

Another object is to stabilize flow control members to restrict the extent to which such control members can move off-center inadvertently, particularly with relatively thin diaphragms that are needed for flow control valves with relatively low cracking pressures.

A further object is to achieve stabilization without diaphragm deformation, which can distort the seal of the diaphragm against its seat. A related object is to overcome the disadavantages that occur when a diaphragm is held in place by a transverse bar that extends completely across a valve body, and opposite a triangular support which partially deforms the center of the diaphragm in an attempt to restrain the diaphragm against inadvertent sideways movement.

Yet another object is to provide a facility for acting upon a flow control member by using other than fluid pressure. A related object is to permit a user to actuate a control member the independently of fluid pressure, in preparation for anticipated fluid flow. Still another related object is to stabilize low cracking pressure valves. A further object is to stabilize diaphragms of relative thinness.

Still another object is to maintain a flow control member in its open position for a prescribed interval of time independently of whether fluid flow is present.

A still further object is to facilitate the use of flow control devices with fittings that vary in tolerance. A related object is to employ flow control valves with a variety of fittings.

Still another related object is to permit a flow control valve that is suitable for a particular fitting to function in the same way with a different fitting, even if the fitting is not of the same general type, and despite tolerance variations.

A still further object is to achieve greater reliability over valve operation than is achievable by clamped diaphragms and duck-bill valves.

Yet another object is to achieve precision control at reduced cost and simplification, particularly for low cracking pressure diaphragms which are relatively thin.

An important object of the invention is to eliminate the need for needle usage at injection sites, while permitting needle usage if that is desired. A related object is to maintain sterility at injection sites that are operated without needles, while simultaneously permitting such sites to be used with needles.

An additional object of the invention is to improve the performance of injection site valves.

SUMMARY OF THE INVENTION

In accomplishing the foregoing and related objects the invention provides a flow control device which includes an inlet for the flow of fluid, and an outlet which is connected to the inlet and disposed to serve as a conduit for flow into the inlet. Provision is made between the inlet and outlet for controlling flow, for example by a movable member having a central portion and sealing the inlet, with the movable member controlling flow. The invention also uses a flexible diaphragm that is stabilized by a cantilever which does not deform the diaphragm.

The invention also provides an instrumentality for permitting the activation of the movable member, such as a bell-shaped member, by an instrumentality external to the flow control device. The instumentality can engage and depress the control member.

In accordance with one aspect of the invention the control member can be a diaphragm bowed under pressure into the inlet channel. One side of the diaphragm is bowed by a prong extending in the axial direction of the inlet channel, and another side of the diaphragm is contacted by the cantilever. The diaphragm also can be positioned by the prong against an annular seat and be movable away from the annular seat.

The cantilever is flexible and limits the lateral movement of the diaphragm without deforming it. The seat for the diaphragm desirably has a circumferential skirt that further limits the lateral movement of the diaphragm.

In accordance with another aspect of the invention the diaphragm is positioned by the prong against an annular seat and is disposable away from the annular seat. The diaphragm can be spaced from buttresses to limit the movement of the diaphragm. The buttresses advantageously are equally positioned and circumferentially arranged with respect to the diaphragm. The inlet channel has opposite ends, of which one end is connected to a subordinate channel extending from a base and an injection site is included at the junction of the subordinate channel and the base.

In accordance with yet another aspect of the invention the the flow control device has a channel for the flow of fluid, a branch channel angularly disposed with respect to the first channel to serve as a conduit for at least a portion of the flow into the branch channel. A flow control member at the convergence of the branch and first channels controls the flow from the first channel with respect to the branch channel.

In accordance with yet another aspect of the invention one of the channels is terminated in a base, and another channel is terminated in a cap. The device is formed as a two-part member with the first part including a stem of the inlet channel, an outer portion of a branch channel and the cap of an injection site. The second part of the device includes a stem of the outlet channel, the remaining portion of the branch channel and the base of the injection site.

In a method of directionally controlling the flow of fluid by the invention, the steps include engaging a plug that seals an inlet channel, and controllably depressing the plug to permit the flow of fluid into an outlet channel. Where a diaphragm is included, it can be stabilized by a flexible cantilever. A branch channel can be connected to an inlet channel for serving as a conduit for at least a portion of the flow in the inlet channel. Flow from the inlet channel into the branch channel can be controlled by applying peripheral pressure to the diaphragm which is bowed into the inlet channel.

In a method of fabricating a flow control device in accordance with the invention, the steps include molding a first member of the flow control device, including a seat for a fluid pressure control diaphragm; molding a second member of the flow control device, including a support for the control member; inserting the control member into the first member with respect to the seat; and joining the second member to the first member against the support for the control member.

In a method of controlling fluid flow, the steps can include introducing fluid into an inlet channel; and controlling the flow of the fluid from the inlet channel into an outlet channel by cantilever stabilization of a diaphragm which is bowed under pressure into the inlet channel.

A flow control device pursuant to the invention includes a first channel for the flow of fluid, a branch channel connected to the first channel to serve as a conduit for at least a portion of the flow, and a diaphragm positioned at the convergence of the branch and first channels for controlling the flow from the first channel into the branch channel.

The first channel has a central axis and the flow control member is placed under pressure. Where the control member is a diaphragm, it is pressured along a central axis and extends against a flexible cantilever. The flow control member can be positioned with respect to radially extending buttresses which limit the extent to which pressure can force the flow control member away from its seat.

The buttresses advantageously are equally distributed with respect to the circumference of the associated channel. In addition, when the radially extending buttresses are positioned opposite a ring seat, with the flow control member extending beyond the seat.

The buttresses can be positioned in a closed end of a channel, extending radially while being circumferentially disposed.

One channel can be terminated in an injection site with a depressible plug.

In a method of directionally controlling the flow of fluid, the steps include providing a first channel for the flow of fluid; providing a branch channel, connected to the first channel, for serving as a conduit for at least a portion of the flow in the first channel; and controlling the flow from the first channel with respect to a branch channel by a displaceable flow control member. When the flow control member is a diaphragm, it is restricted from lateral displacement by a stabilizing cantilever. The inlet can be an injection site near a junction with the branch channel to permit the flow of fluid to an outlet.

A flow control device of the invention can include a first channel for the control of fluid; a ring seat within the first channel; a cantilever within the first channel; a control diaphragm in tangential contact with the ring seat and the cantilever. Radially extending buttresses can be positioned opposite the ring seat, with the diaphragm between the buttresses and the ring seat. The radially extending buttresses can be circumferentially disposed about the first channel, and extend on both sides of the tangential contact of the diaphragm with the ring seat.

In a method of controlling fluid flow, the steps include introducing fluid into a first channel; diverting the fluid into a branch channel, with the flow of fluid from the first channel into the second channel controlled by acting against a flow control member, which is under pressure.

DESCRIPTION OF THE DRAWINGS

First Embodiment

FIG. 1A is a side view of a directional flow-control valve and coupling device with an injection site plug in accordance with the invention;

FIG. 1B is a top view of the flow control device of FIG. 1A showing the stabilizing cantilever used in the device of FIG. 1A;

FIG. 1C is a key diagram showing the relationship between FIG. 1D and FIG. 1E;

FIG. 1E is a sectional view of the flow control device of FIGS. 1A and 1B taken along the lines E—E in FIG. 1B;

Second Embodiment

Figure 2A:
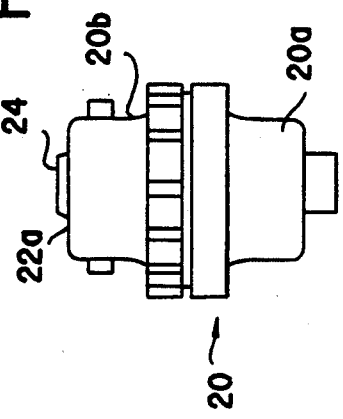
Figure 2B:
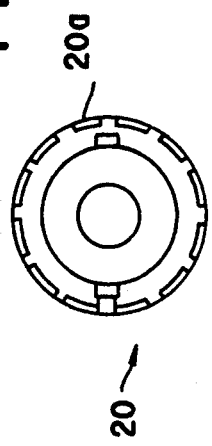
Figure 2D:
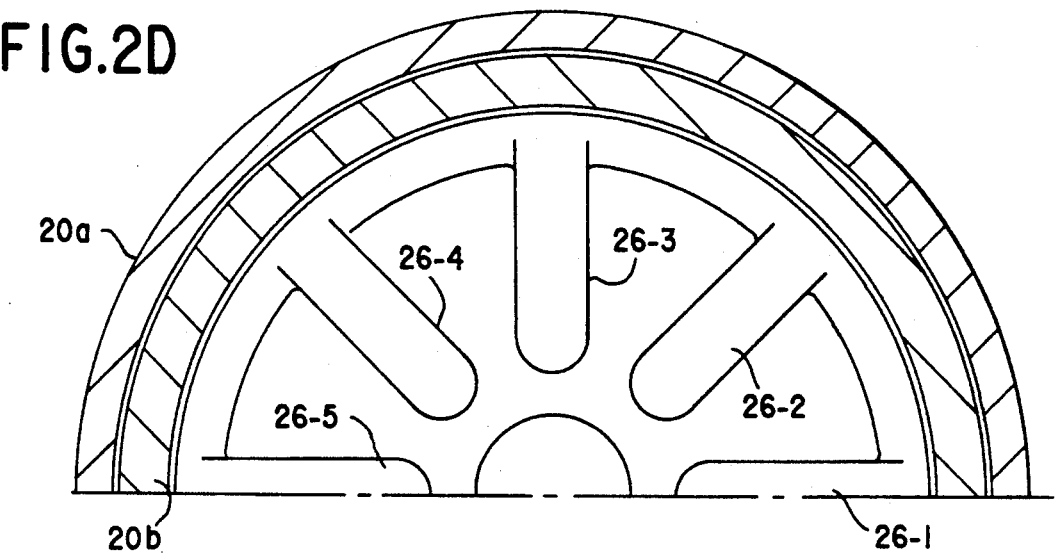
Figure 2E:
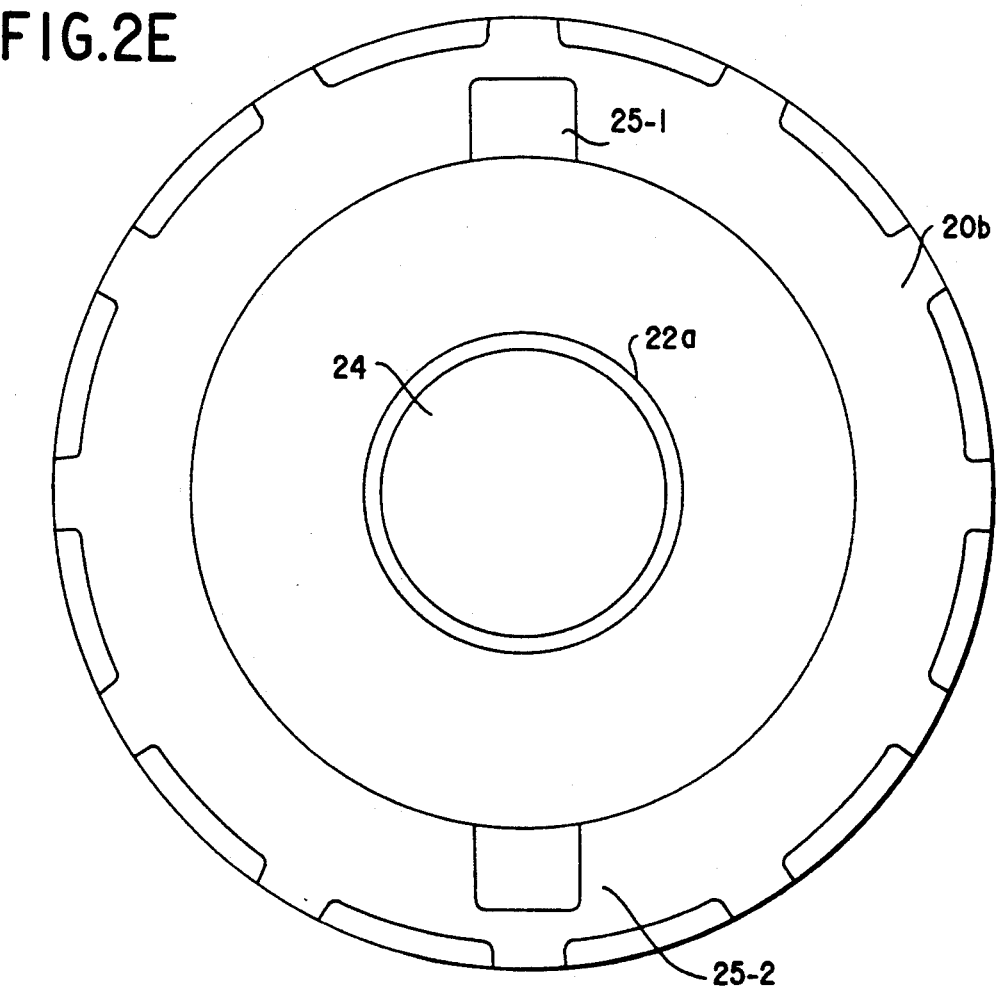
Figure 2G:
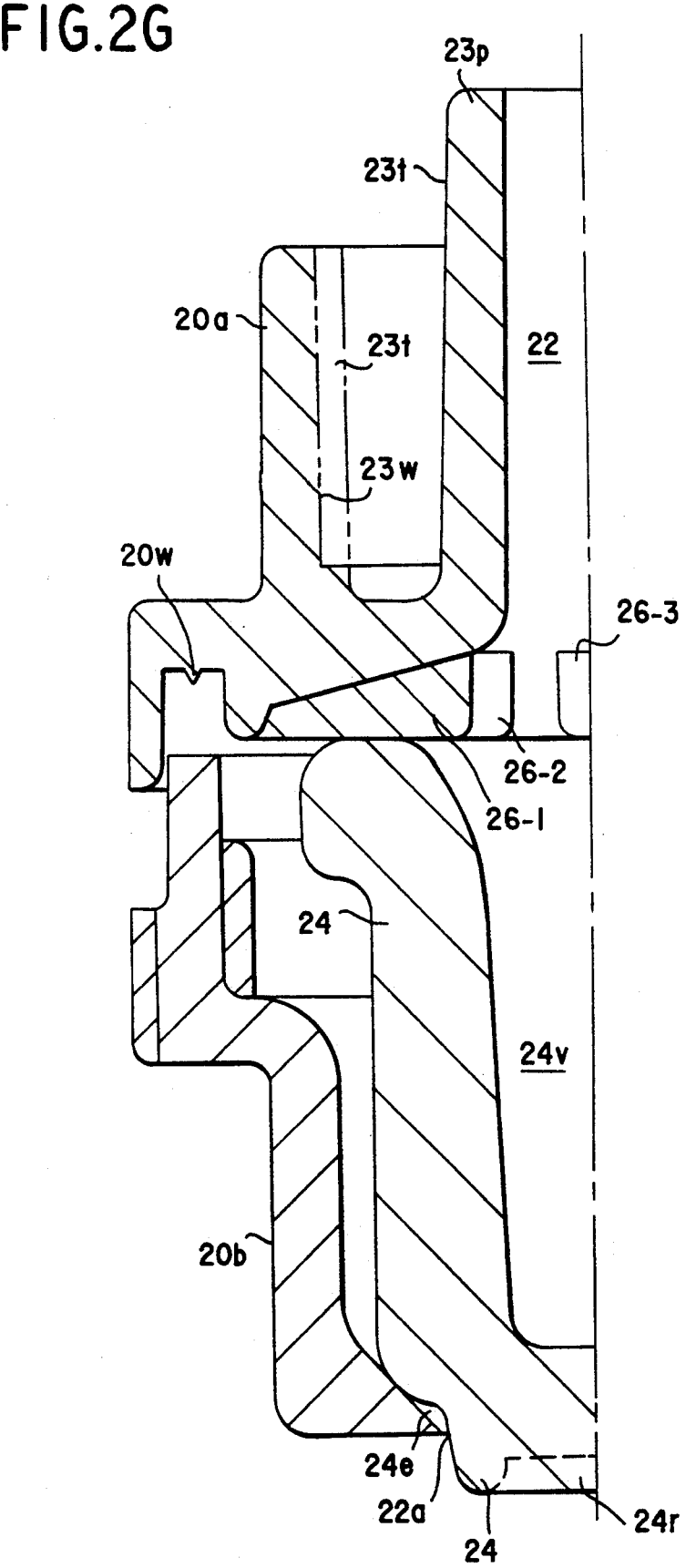

FIG. 2A is a side view of an alternative flow-control valve with an infusion site in accordance with the invention;

FIG. 2B is a top view of the flow control device of FIG. 2A;

FIG. 2C is a cross-sectional view of the alternative infusion site device in accordance with the invention taken along the lines C—C of FIG. 2B;

FIG. 2D is a sectional view of the infusion site device of FIG. 2C taken along the lines D—D;

FIG. 2E is an enlarged top view of the infusion site device of FIG. 2B;

FIG. 2F is an enlarged bottom view of the infusion site device of FIG. 2A;

FIG. 2G is a partial assembly view of the infusion site device of FIG. 2C;

Third Embodiment

Figure 3A:
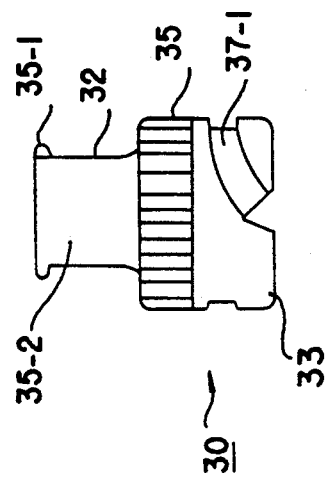
Figure 3B:
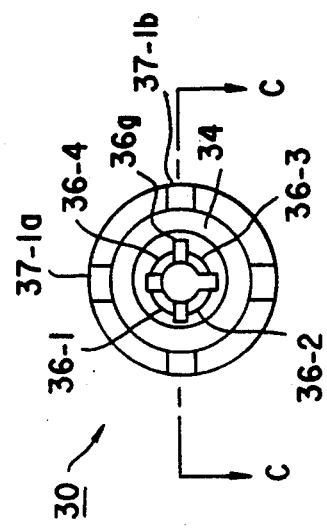
Figure 3C:
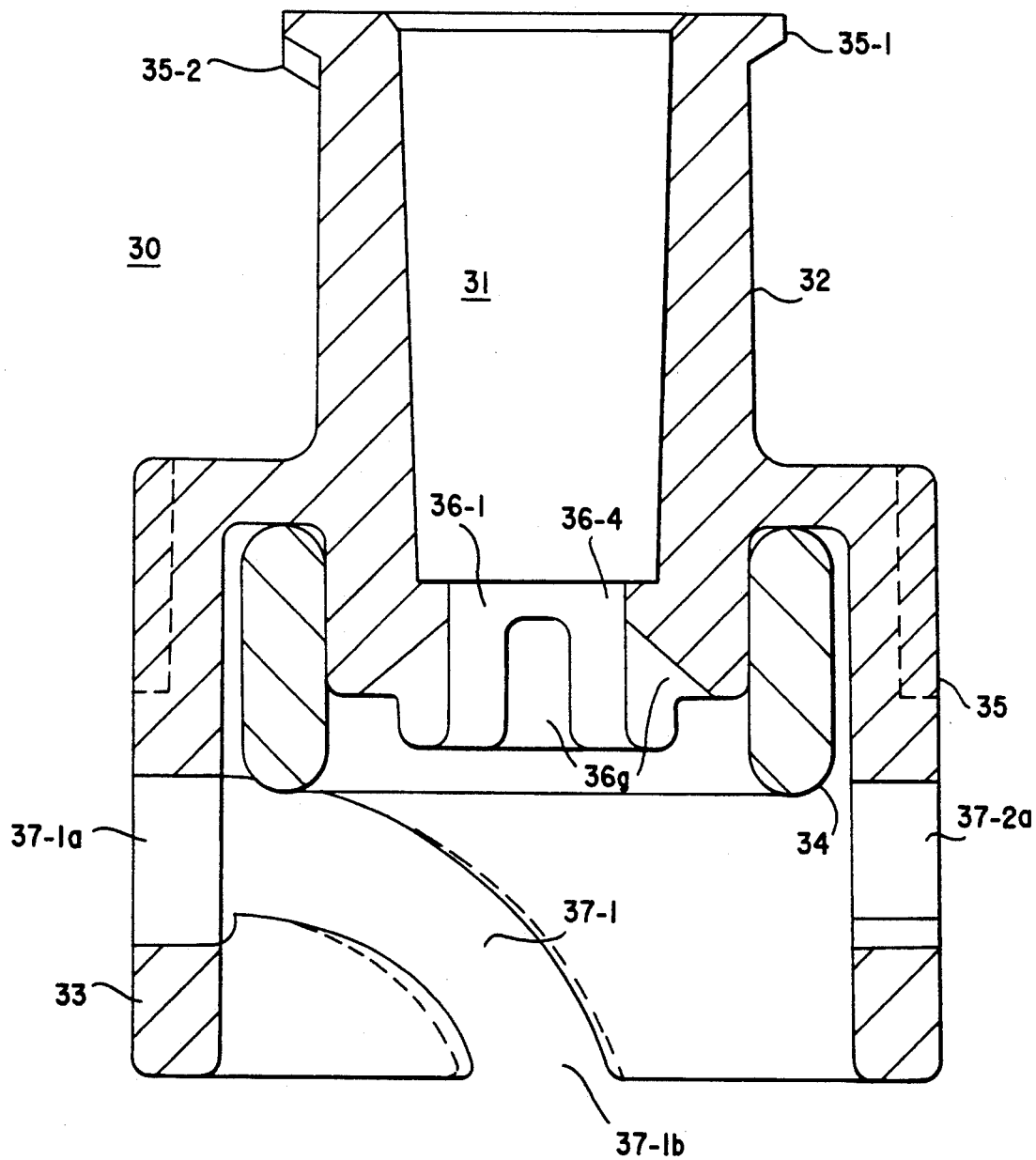
Figure 3F:
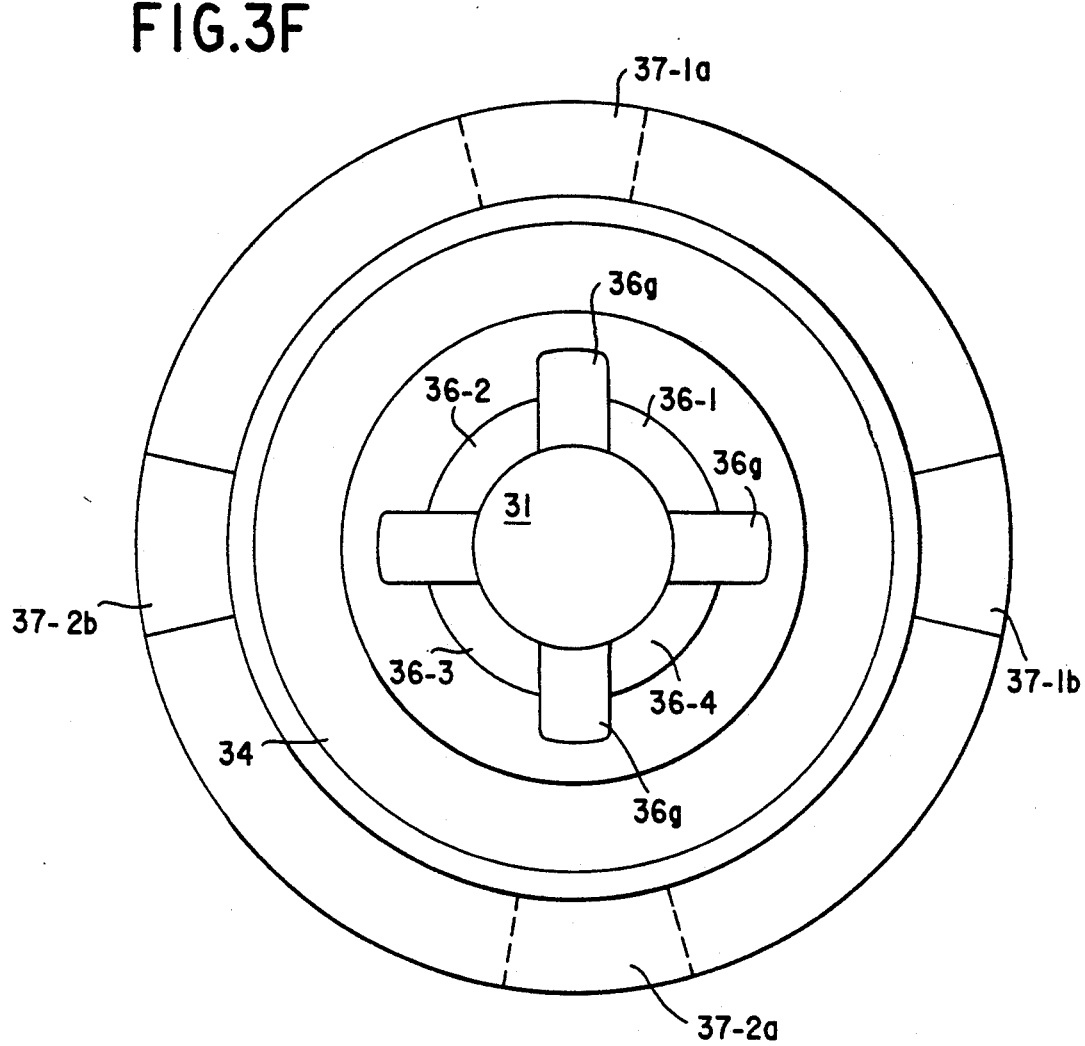
Figure 3G:
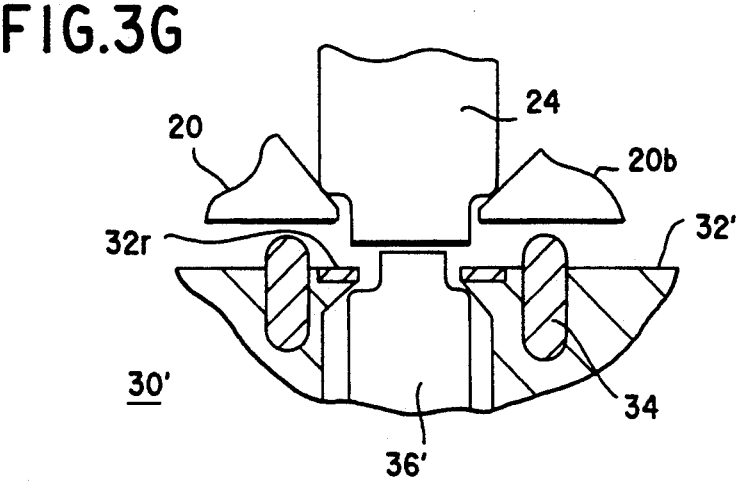

FIG. 3A is a side view of a fitting in accordance with the invention for actuating the infusion site device of FIGS. 2A and 2B;

FIG. 3B is a bottom view of the actuator fitting of FIG. 3A;

FIG. 3C is a cross-sectional view of the infusion site activator device in accordance with the invention taken along the lines C—C of FIG. 3B;

FIG. 3D is a wall fragment of the infusion site activator device of FIG. 3A taken along the lines D—D of FIG. 3E;

FIG. 3E is a top view of the infusion site activator device of FIG. 3A;

FIG. 3F is an enlarged bottom view of the infusion site activator device of FIG. 3B;

FIG. 3G is a partial sectional view of an alternative infusion site activator to prevent flow though the activator when disengaged from an injection site;

Additional Embodiments

Figure 4A:
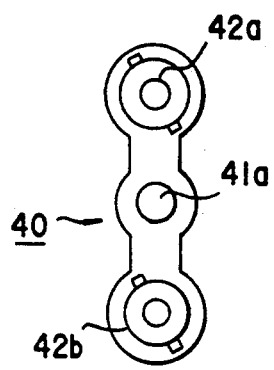
Figure 4B:
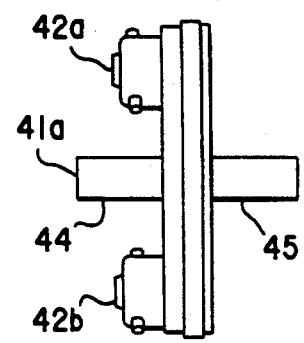
Figure 4C:
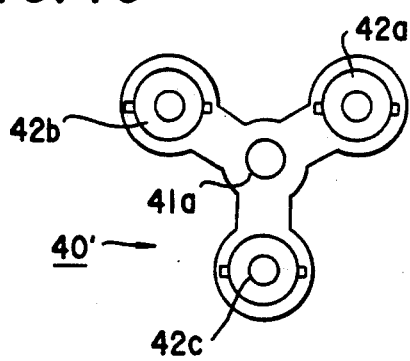
Figure 4D:
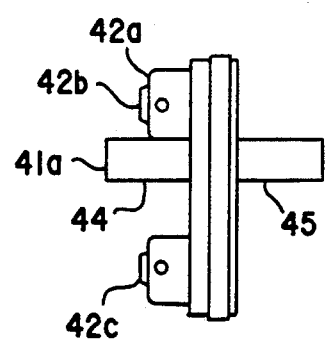

FIG. 4A is a top view of a dual port infusion site device formed by coupling two devices of the kind shown in FIG. 2A to a common throughput channel;

FIG. 4B is a side view of the dual port infusion site device of FIG. 4A;

FIG. 4C is a top view of a tri-port infusion site device formed by adding a third port to the device of FIG. 4A; and FIG. 4D is a top view of a tri-port infusion site device of FIG. 4A.

DETAILED DESCRIPTION

(a) First Embodiment of the Invention

With reference to the drawings, a coupling device 10 in accordance with the invention is shown in side view in FIG. 1A, and in top view in a FIG. 1B. The device 10 is formed by a base 10b and a cap 10c. The cap 10c contains inlets 11a and 12a, respectively for a flow channel 11 and an auxiliary flow channel 12.

In FIGS. 1A and 1B, the inlet 12a of the auxiliary flow channel 12 serves as an infusion or injection site. The site 12a can be used for the needless infusion of liquids, as described below, or the site 12a can be used for conventional injection by needle. Either the channel 11 or the channel 12 may be an inlet channel.

The cap 10c also includes a coupling mount 14 that receives a flow input connection (not shown in FIG. 1A), such as tubing or a Luer fitting. In the latter case, the mount is adapted accordingly. Similarly, the base 10b includes a coupling mount 15 for a flow output connection.

Figure 1D:
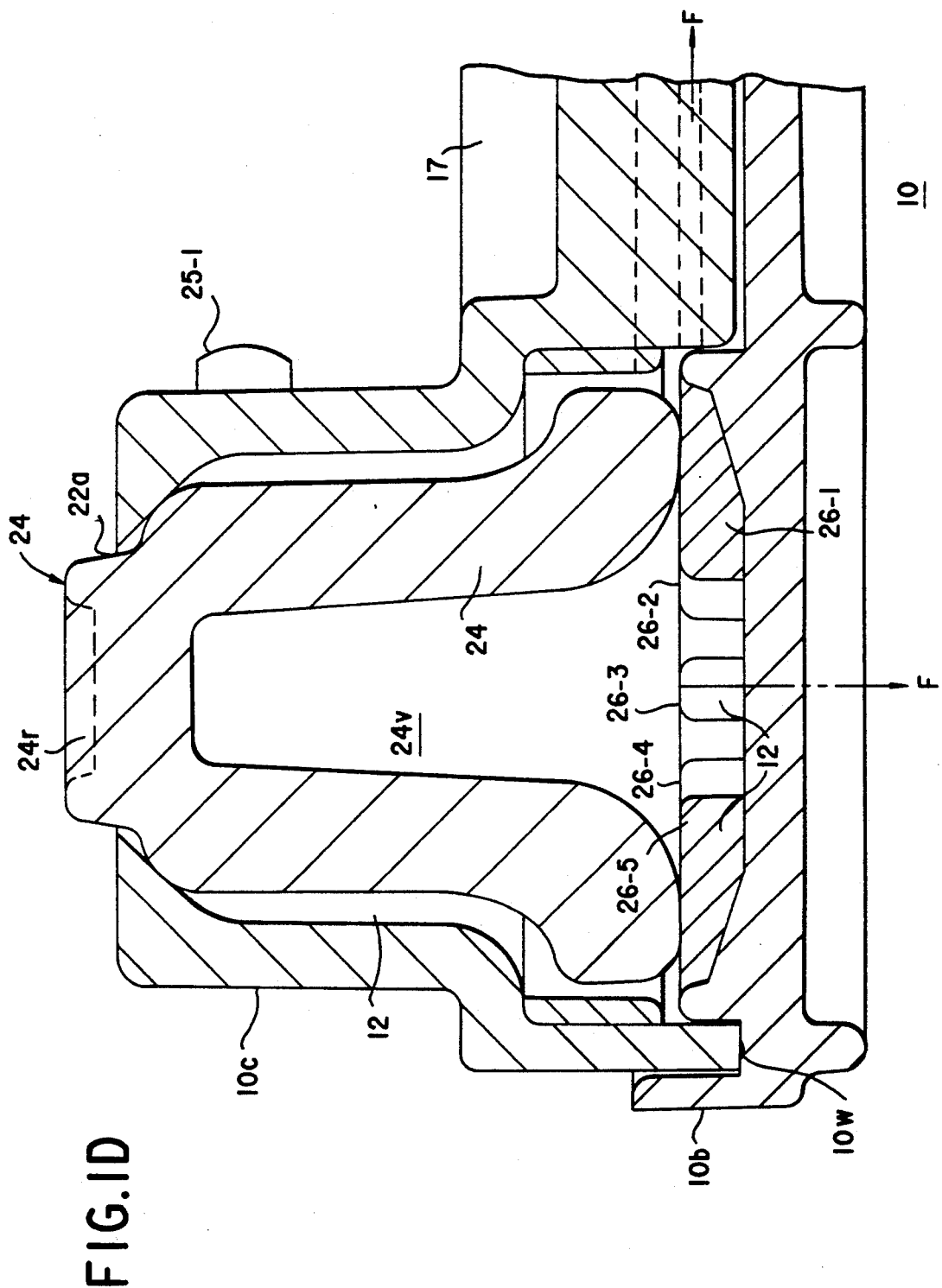
FIG. 1D is a sectional view of the flow control device of FIGS. 1A and 1B taken along the lines D—D in FIG. 1B.

Flow from the respective channels 11 and 12 is selectively combined in an output channel 13 in accordance with the operation of a control diaphragm 10d shown in FIG. 1E. FIG. 1E gives details of the structure between the mounts 14 and 15, and is related by FIG. 1C to FIG. 1D which gives details for infusion site 12a.

As indicated in FIG. 1E, the diaphragm 10d seals the channel 11 when there is upward flow in the channel 13. This kind of diaphragm operation is commonly provided by a check valve, but in FIGS. 1A and 1B is provided by the multifunctional coupling structure 10. In channel 11, when there is downward flow through the housing 14, the diaphragm 10d is unseated. Conversely, when pressure against the member 10d is withdrawn, it is reseated.

In order to properly seat the diaphragm 10d on a ring seat 10r when there is no downward flow, the base 10b includes a prebiasing prong 10p on a platform 10k. "Prebiasing" means that there is a small force, i.e., bias, exerted against the diaphragm 10d by the prong 10p when the diaphragm is in its equilibrium position.

In addition to having the diaphragm 10d opened by flow, the invention provides a flexible cantilever 14c which stabilizes the diaphragm 10d, particularly when it is relatively thin, and restricts the extent to which the diaphragm can be shifted sideways. The cantilever 14c is shown in sectional view in FIG. 1E, and a view from above is shown in FIG. 1B, and in enlargement in FIG. 1G.

Figure 1F:
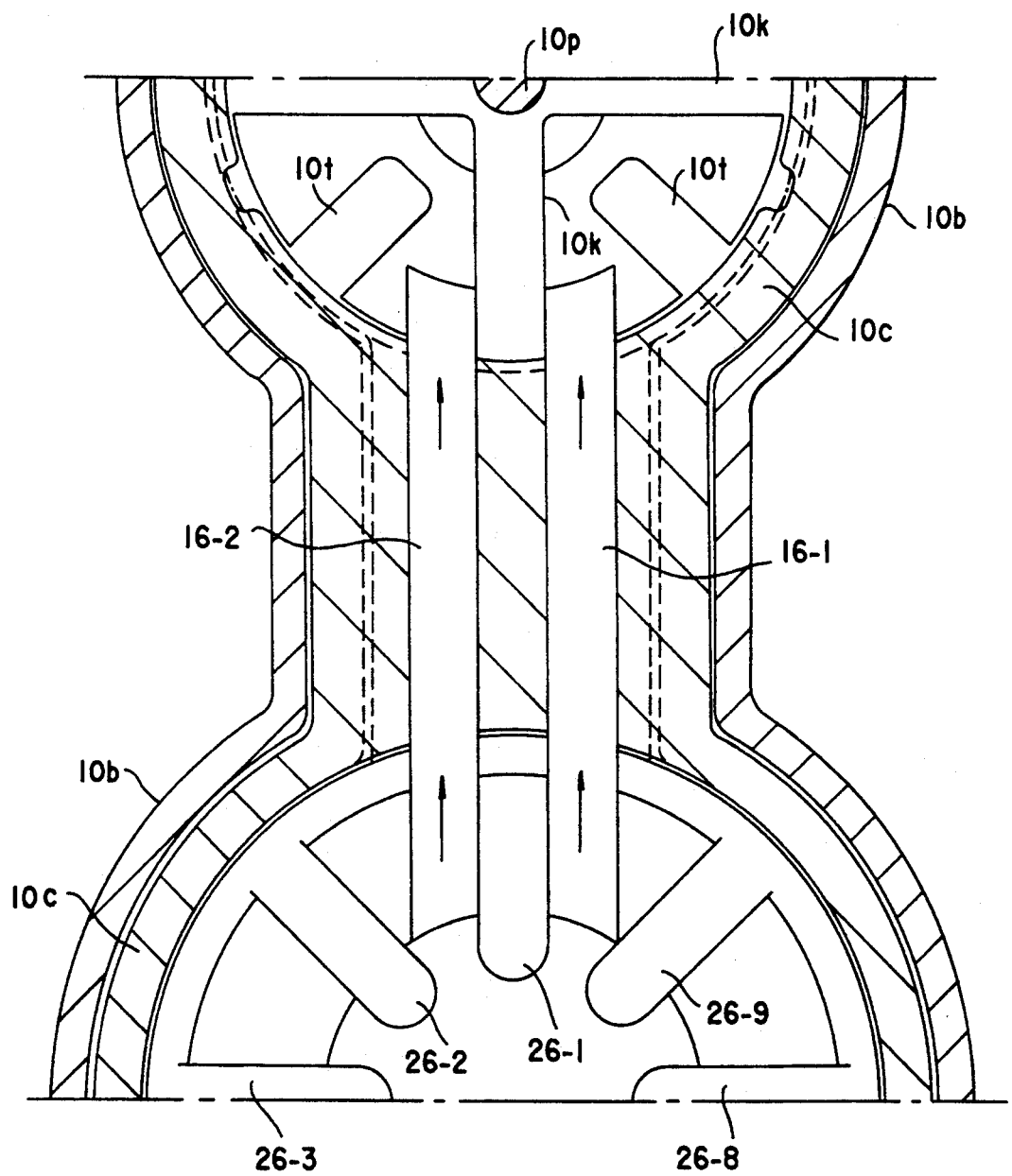
FIG. 1F is a section of the valve of FIGS. 1A and 1B taken along the lines F—F of FIGS. 1D and 1E.
Figure 1G:
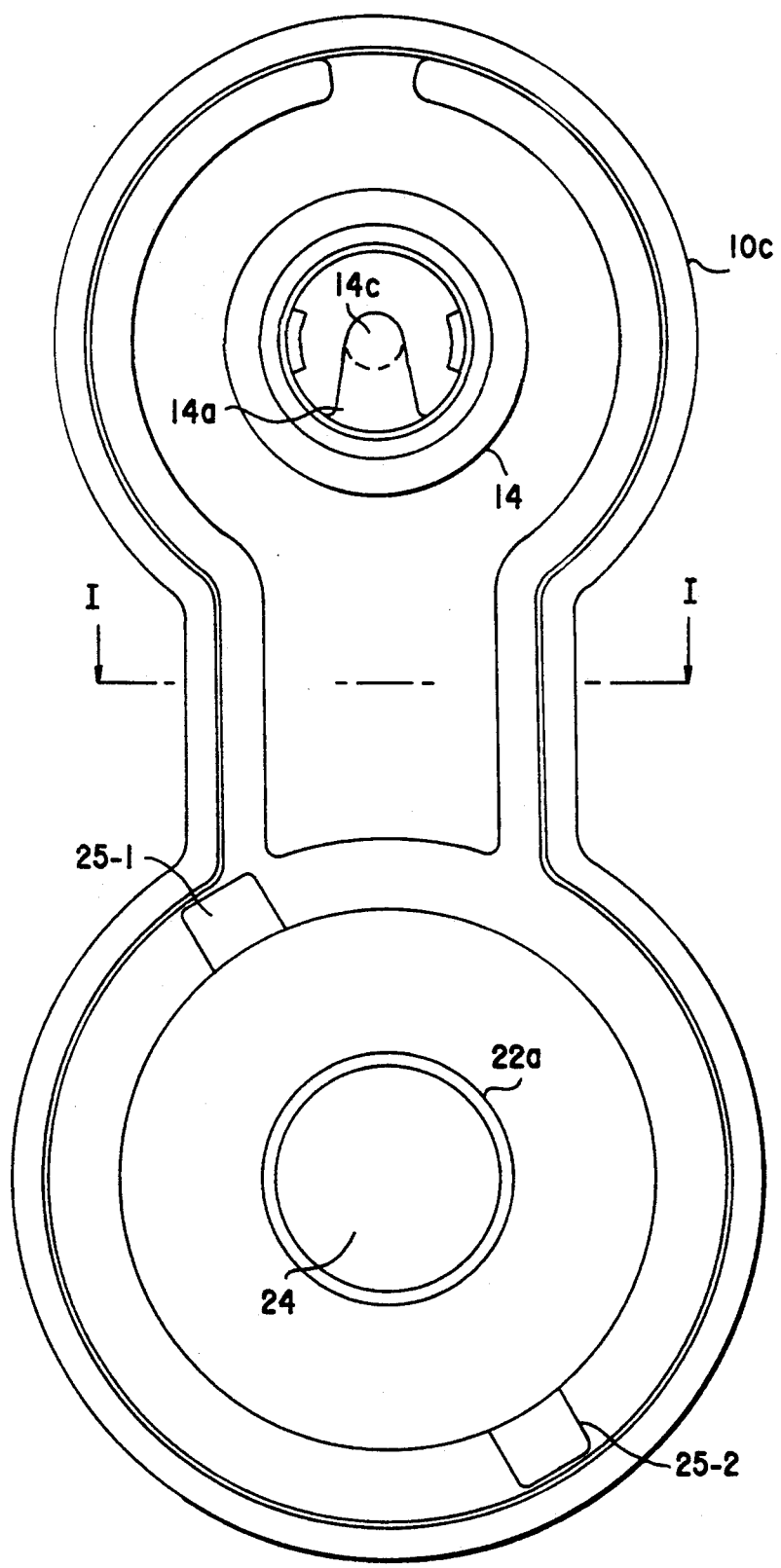
FIG. 1G is an enlarged top view of the valve of FIGS. 1A and 1B.
Figure 1H:
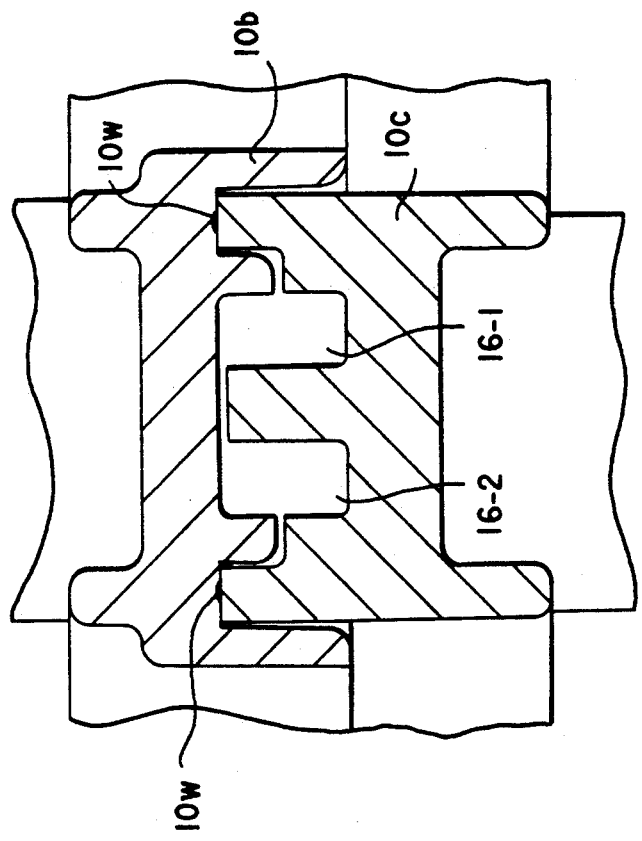
FIG. 1H is a cross-section of the valve of FIGS. 1A and 1B taken along the lines H—H of FIG. 1G.
Figure 1J:
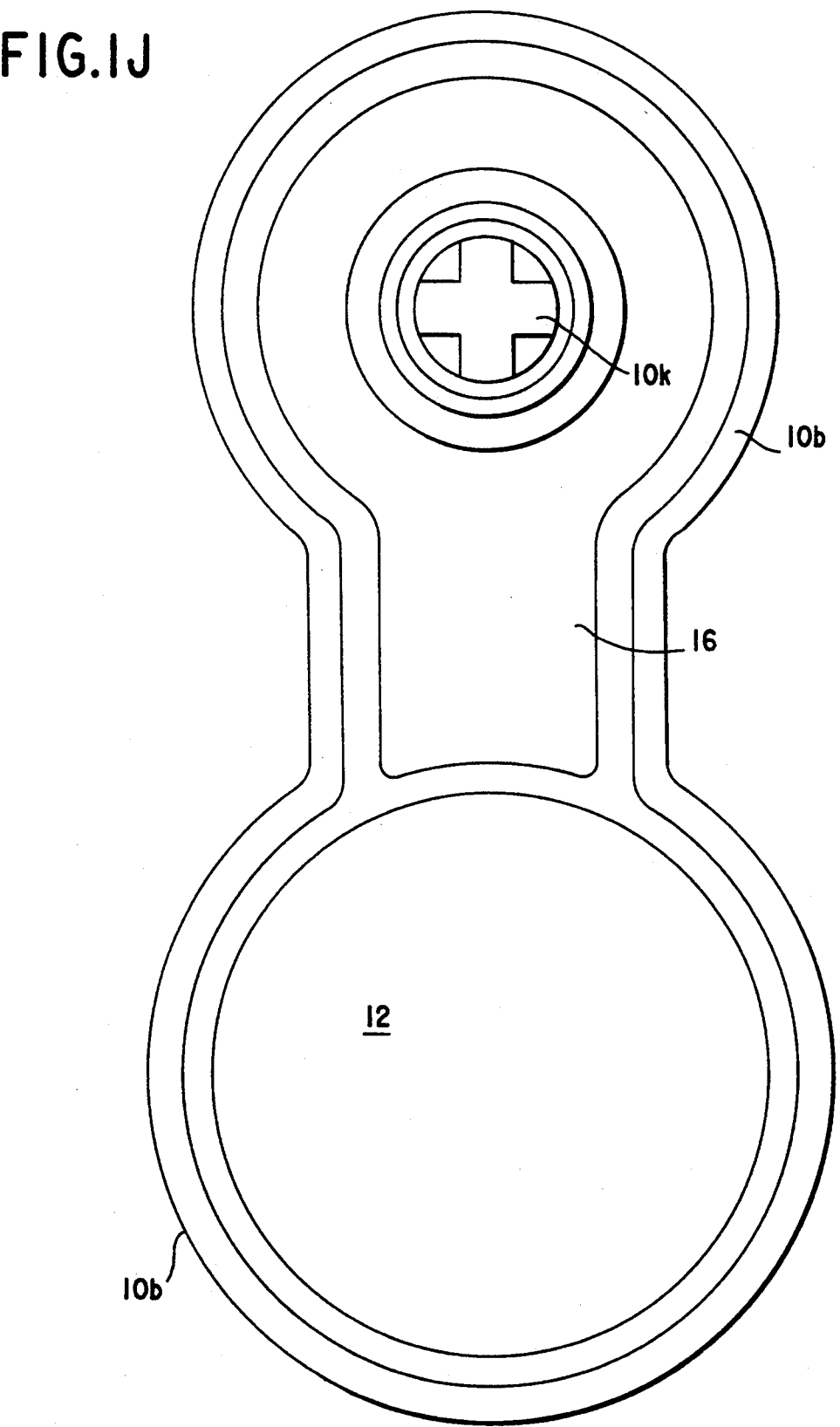
FIG. 1J is an enlarged bottom view of the valve of FIGS. 1A and 1B.

With respect to the cantilever 14c as shown in FIGS. 1B, 1E and 1G, it extends into the channel 11 from a side wall 14w by an arm 14a. The arm 14a of the cantilever 14c terminates in a prong 14p that makes touching contact with the diaphragm 10d. The cantilever is proportioned to provide spring tension against the diaphragm 10d without deforming it. Any such deformation could distort the diaphragm and interfere with its seating against the ring seat 10r. The cantilever is needed only for relatively thin diaphragms, since the structure relative to the ring seat 10r is otherwise suitable for preventing undesried diaphragm shifts. In essence the cantilever 14p acts to stabilize a relatively thin diaphragm against inadvertent lateral shifts in position with respect to the prong 27.

Structurally the disc 10d has opposed surfaces and the prong 10p is mounted on cross arms 10k affixed to the lower body element 10b as detailed in FIG. 1F. In addition there are lateral extensions or buttresses 10t to assure that when the diaphragm disc 10d is open, there will be an adequate passage for liquid flow about the peripheral edge of the disc 10d.

The channel 12 is an infusion or injection site for the introduction of a substance to be mixed with fluid flowing in the channel 13. Details of the injection site member are discussed in conjunction with FIGS. 2A throught 2E.

The combination infusion site and the check valve in FIGS. 1A and 1B achieves a number of advantages. The close proximity of the site and valve prevents any retrograde flow and improves purging. This is important in the case of drugs that require minimum diluent, or that must be administered quickly to a patient. In the case of viscous and highly dense drugs that flow from intravenous tubing, a considerable amount of time and fluid are required in order to purge the drug out of tubing. It is important to minimize any stagnant area where drugs or air can collect. This avoids air entrapment.

The component elements of the device 10 are joined, for example, by ultrasonic welding. Upon assembly the upper tip of the prong 10p applies pressure to the diaphragm or disc 10d, which tends to be held in position against the cantilever 14c. Preferably the pressure by the prong 10p, coupled with the action of the cantilever 14c, tends to restrain the disc from side-to-side movement.

A horizontal passageway within the parts 10b–10c extends to the injection site member 24 from the junction of the inlet sleeve 14 and the outlet sleeve 15. Fluid can flow vertically downward around the plug 24 for needleless infusion, or through the plug for needle injection, into the passageway 16 extending between the plug 24 and the diaphragm 10d, and is combined with any flow around the diaphragm 10d, then downwardly through the outlet sleeve 15 As a result, tubing attached to the inlet sleeve 14 of the housing, and to the outlet sleeve 15 of the housing are approximately parallel to one another.

Since the tubing generally hangs vertically, the injection site 24 generally is positioned near the top of the cap 10c where it is easily accessible to medical personnel. After an intravenous solution enters the site 24, it makes an approximately right-angle turn and moves directly across the bottom of the diaphragm 10d. The fluid flow then forces substantially all air below the site 10d into the outlet sleeve 15. The injection site is thus self-priming.

In a number of prior art injection sites, particularly those with sleeve stoppers, cavities located at the centers of the stoppers prevented self-priming. With a sleeve stopper, even a liquid stream directed across the bottom of the stopper cannot expel air located within a cavity. Air has to be removed in such a case by inverting the injection site, while manually tapping the housing.

As indicated by the cross-sectional view of one embodiment of the injection site 24 shown in FIG. 1D, the ease of accessibility to the entire exposed surface promotes sterility. The same considerations apply to the similar injection site of FIGS. 2A and 2B. Prior art injection sites with stoppers recessed below the tops of injection sites allow antimicrobial agents to accumulate in puddles on the tops of stoppers. Particulate matter may also collect on recessed stoppers and be transmitted from the injection site to intravenous solution when the stopper is pierced by a needle. A raised site, guards against the presence of microbial agents.

In addition, as shown in FIG. 1D, the injection site provides a perferred target for injection. The housing 10c for the injection site is molded as one unit and forms a suitable closure for the site. In addition, the unitary housing 10c extends to the inlet sleeve 14. The Housing 10c also forms a cover 17 for the passageway 16 that extends from the diaphragm 10d to the vicinity of the base of the site 24.

In completing the structure 10 by ultrasonic welding, ultrasonic welds are at the base of a trough which extends completely around the upper portion of the housing 10b. Because the device 10 is formed by a two-part housing, assembly of the device is relatively simple as compared with he complexity of assembly required for the prior art. The assembly is readily accomplished by inserting the plug 24 into the cap of the member 10c, and simultaneously inserting the diaphragm 10d against a ring seat of the sleeve 14. The second member 10b is then seated against the member 10c and the ultrasonic welding accomplished. By contrast with prior directional flow control valves, the diaphragm 10d is freely movable and is not compressively pinned to the valve structure. The free movability of the diaphragm 10d assures positive seating under a prescribed amount of bias, i.e., equilibrium pressure provided by the central pin 10p. Once there is flow from the infusion site, it is guided by the dual passageway 16-1 and 16-2 to the outlet sleeve 15.

A cross-sectional view of FIG. 3H taken along the lines H—H of FIG. 1G shows the dual channel passageway.

(b) Second Embodiment of the Invention

An alternative flow control device 20 in accordance with the invention is shown in FIG. 2A. In the device 20, there is a housing with two parts 20a and 20b. The part 20a includes a flow control member taking the form of a plug 24. The plug 24 is depressed externally of the device 20 to permit opening of the inlet 22a. Generally, the device 20, like the device 10 of FIG. 1A, can be used for continuous intravenous fluid administration to a patient.

When therapy of a patient requires supplemental intravenous medication, or other intermittent fluid administration, the device of FIG. 2A is modified by including a branch, similar to that of FIG. 1A, so that a syringe or other injection apparatus can be used to insert medication into the intravenous fluid. This is accomplished by inserting an injector into a branch channel. Since an intravenous solution may be administered for lengthy periods, any closure used in the branch channel desirably should withstand numerous injections, even under high pressure.

The housing 20b accommodates the flexible plug 24, as shown in detail in FIG. 2C. The plug 24 is approximately bell-shaped and can have a longitudinal split (not shown) to provide additional flexibility when the plug 24 is engaged. In order to allow for tolerance variations in the valve housing with respect to the engagement fitting, such as the fitting 30 of FIG. 3A, the upper edge 24e of the plug 24 is beveled as indicated in FIG. 2C. Thereafter, when the valve of FIG. 2C is to be opened, the fitting is pushed against the plug 24 to depress it and clear the opening 22a around the sides 24s into the channel 22. This allows flow as indicated by the arrows in FIG. 2C. When the plug 24 is used in the valve of FIG. 2A, the top of the housing 20b holds the plug 24 in position.

The use of a flexible plug 24 is important to assure that the fitting, e.g., 30 of FIG. 3A, will unseat the inlet to the infusion site and simultaneously act upon the plug.

The coupling of the valve 20 to another devise is illustrated in FIG. 2C by a Luer adaptation with respect to the body portion 2a of FIG. 2A. The outer end of the body portion 20a has a projection 23p which is surrounded by threads 23t of the wall 23w. It is apparent that when the Luer termination, with a Luer taper 23t is threaded on a receptacle, the tip of the fitting engages an inlet.

(c) Third Embodiment of the Invention

In order to activate the flow control device of FIG. 2A the invention also provides the fitting 30 shown in side view in FIG. 3A and in bottom view in FIG. 3B.

As indicated in the cross sectional view of FIG. 3C, the fitting 30 is formed by a neck 32 extending from a mount 33. The neck 32 encloses a passageway 31 for the throughflow of fluid. The outflow portion of the neck 32 terminates in prongs 36-1 through 36-4, as shown in FIG. 3B, with only prongs 36-1 and 36-4 visible in FIG. 3C. The individual prongs 36-1 through 36-4 are separated by grooves 36g. The inlet portion of the mount 32 includes Luer fittings 35-1 and 35-2. The mount 33 includes channels 37-1 and 37-2, shown in FIGS. 3A and 3B, with only channel 37-1 visible in FIG. 3C. Each of the channels 37-1 and 37-2 commences at an inlet in the base of the mount 33 and terminates in an opening in the side wall of the mount 33. Thus, the channel 37-1 shown in FIG. 3C and in FIG. 3B commences at an inlet 37-1b and terminates in an opening 37-1a. The purpose of the channels 37-1 and 37-2 is to engage projections, such as the projections 25-1 and 25-2 of FIGS. 1D, 2C, 1G and 2E. As a result, the application of rotational force to the mount 33 while the channels 37-1 and 37-2 engage the projections 25-1 and 25-2 brings the prongs 36-1 through 36-4 into contact with the plug 24 of FIGS. 1D and 2C. Simultaneously an elastomeric washer 34 within the mount 33 an encircling the prongs 36-1 through 36-4 seals the inlets 22a of FIGS. 1D and 2C. The engagement operation is facilitated by the use of the knurled outer ring 35 of the mount 33. Details of the knurled ring 35 are shown in FIG. 3E which also illustrates the range over which the channel 37-1 extends in FIG. 3D. An enlarged bottom view of the fitting 31 is shown in FIG. 3F.

An alternative infusion site activator 30' is illustrated in a partial sectional view of FIG. 3G for preventing flow from the activator when disengaged from an injection site, such as the site 20 also shown in partial sectional view in FIG. 3G. As in the case of the fitting 30 of FIG. 3C, the alternative fitting 30' includes a sealing ring 34, but the channel 31 is provided with a plug 36' similar to the plug 24 of FIGS. 1D and 2C. In addition, the lower portion of the neck 32' terminates in a recessed surface 32r within the sealing ring 34. The recessed surface 32r is similar in configuration to the prong groove arrangement 36g-36 of FIG. 3F.

The partially illustrated infusion site device 20 of FIG. 3G includes the plug 24 and the wall 20b which is shown in detail in FIG. 2C.

In operation of the alternative actuator 30', the sealing ring 34 is brought into engagement with the surface 20b of the device 20. After the seal is effectuated, the plug 24 depresses the plug 36' and thus creates a passageway for the flow of fluid through the fitting 30'. Further engagement between the fitting 30' and the device 20 brings the recessed surface 32r into contact with the tip of the plug 24, depressing it and opening a channel into the device 20 so that fluid can flow around the plug 36' into the recesses of the surface 32r and then around the plug 24. When the fitting 30' is uncoupled from the device 20, the plug 36' is reseated, preventing any further flow of fluid.

(d) Additional Embodiments

The embodiments of FIGS. 1A and 1B, and FIGS. 2A and 2B are single port infusion devices. The invention also includes multiple port infusion devices as shown in FIGS. 4A through 4D.

In particular, the device 40 of FIGS. 4A and 4B has 2 ports 42a and 42b. These ports are circumferentially mounted with respect to inlet and outlet housings 44 and 45. The ports 42a and 42b are similar to the ports 12a of FIGS. 1A and 1B and the port 22a of FIGS. 2A and 2B. The housings 44 and 45 may or may not include the flow control diaphragm 10d of FIG. 1E. In general, the multiport infusing devices 40 and 40' of FIGS. 4A through 4D will omit the diaphragm 10d.

A tri-port infusion site device similar to that of FIGS. 4A and 4B, except for having a third site 42c, is shown in FIGS. 4C and 4D.

Other aspects of the invention will be apparent to those of ordinary skills in the art.

What is claimed is:

1. A flow control device for the infusion of fluids comprising
an inlet for the flow of fluid;
an outlet for said inlet and disposed with respect thereto to serve as a conduit for flow from said inlet; and
movable flow controlling means sealing said inlet and having a pierceable central portion for controlling flow by the extent to which the central portion of said movable means is moved away from said inlet; wherein
a first channel for the flow of fluid extends between said inlet and said outlet;
a branch channel is connected to said first channel beyond said moveable means to serve as a conduit for at least a portion of the flow into said first channel; and
a member is positioned at the convergence of the branch and first channels for controlling the flow from said branch channel.

2. A flow control device for the infusion of fluids comprising
an inlet for the flow of fluid;
an outlet for said inlet and disposed with respect thereto to serve as a conduit for flow from said inlet; and
movable flow controlling means sealing said inlet and having a pierceable central portion for controlling flow by the extent to which the central portion of said movable means is moved away from said inlet; wherein
said movable means sealing said inlet comprises a bell-shaped member having a dome and side walls, with said dome extending out of said inlet and said walls straddling said outlet.

3. Apparatus as defined in claim 2 further including means for permitting the activation of the controlling means, after sealing said inlet, by a member external to the flow control device.

4. Apparatus as defined in claim 3 wherein said means for permitting the activation of said controlling means comprises a fitting formed by a neck extending from a mount and enclosing a passageway for the throughflow of fluid, with an outflow portion of the neck terminating in at least one prong for engaging said controlling means.

5. Apparatus as defined in claim 3 wherein said means for permitting the activation of the controlling means by a member external to the flow control device comprises means for sealing said member.

6. Apparatus as defined in claim 2 comprising a plurality of flow control devices having their outlets connected to a common channel;
thereby to provide a plurality of infusion sites for said common channel.

7. A flow control device in accordance with claim 2 further including
(a) a first channel communicating with said moveable means for the control of fluid;
(b) a ring seat within said first channel;
(c) a flexible plunger within said first channel; and
(d) a control diaphragm in tangential contact with said ring seat and said plunger.

8. An injection site valve in accordance with claim 4 which can be used for needleless infusion or needle injection of a fluid, wherein said moveable means is a plug which can be depressed from its seat for needleless infusion, or penetrated by a needle for needle injection, without disturbing said seal.

9. A flow control device as defined in claim 2 wherein
said inlet has an undercut rim;
said controlling means comprising elastomeric means engaging the undercut portion of the rim of said inlet for controlling flow by the extent to which said elastomeric means is displaced away from said rim to create a passage between said rim and said elastomeric means.

10. Apparatus as defined in claim 2 wherein said inlet has a side wall and said moveable means has a shoulder contacting said side wall.

11. Apparatus as defined in claim 2 wherein
said inlet includes an injection site and said outlet is connected to a subordinate channel extending to further flow control means at the junction of said subordinate channel and an outlet channel.

12. Apparatus as defined in claim 2 for controlling fluid flow from said inlet having an entrance, to said outlet having an exit, which comprises:
(1) a stopper sealing the entrance of said inlet; and (2) means for controllably depressing said stopper at said entrance to permit the flow of said fluid to said outlet and out of said exit.

13. The apparatus of claim 12 further including means for connecting said outlet to a common channel.

14. The apparatus of claim 12 wherein the means for controllably depressing said stopper comprises a fitting formed by a neck extending from a mount and enclosing a passageway for the throughflow of fluid, with an outflow portion of the neck terminating in at least one prong for engaging said stopper.

15. The apparatus of claim 12 for directionally controlling the flow of fluid which comprises
    (a) a branch channel connected to said outlet for serving as a conduit for at least a portion of the flow into said inlet; and
    (b) means for controlling the flow from said inlet into said branch channel by applying centralized pressure to said stopper.

16. A flow control device for the infusion of fluids comprising
    an inlet for the flow of fluid;
    an outlet for said inlet and disposed with respect thereto to serve as a conduit for flow from said inlet; and
    movable flow controlling means sealing said inlet and having a pierceable central portion for controlling flow by the extent to which the central portion of said movable means is moved away from said inlet; wherein said inlet includes opposed fittings, further including a mount with a side wall containing opposed grooves engaging said fittings, each groove commencing at an opening in the base of the mount and terminating in another opening in the side wall of said mount.

17. Apparatus as defined in claim 16 further including at least one prong in said mount engaging said moveable means and an elastomeric washer within said mount encircling said prong and sealing said mount to said device.

18. A flow control device for the infusion of fluids comprising
    an inlet for the flow of fluid;
    an outlet for said inlet and disposed with respect thereto to serve as a conduit for flow from said inlet; and
    movable flow controlling means sealing said inlet and having a pierceable central portion for controlling flow by the extent to which the central portion of said movable means is moved away from said inlet; wherein
    an infusion site activator containing a plug and engaging said inlet is adapted for preventing flow from the activator when disengaged from said infusion site, comprising a sealing ring having a recessed surface and in engagement with said device; whereby after sealing is effectuated, said plug is depressed to create a passageway for the flow of fluid through the activator and further engagement between the fitting and the device brings said recessed surface into contact with said moveable means depressing it and opening a channel into said device so that fluid can flow into surface recesses exposed by the movement of said moveable means, so that when the fitting is uncoupled from the device, the said moveable means and said plug are reseated, preventing any further flow of fluid.

* * * * *